United States Patent
Schultz et al.

(10) Patent No.: US 9,216,106 B2
(45) Date of Patent: Dec. 22, 2015

(54) DEVICE AND METHOD FOR THE DELIVERY OF DRUGS FOR THE TREATMENT OF POSTERIOR SEGMENT DISEASE

(75) Inventors: Clyde L. Schultz, Ponte Vedra, FL (US); Jerome J. Schentag, Eggertsville, NY (US)

(73) Assignee: DIRECTCONTACT LLC, Swampscott, MA (US)

( * ) Notice: Subject to any disclaimer, the term of this patent is extended or adjusted under 35 U.S.C. 154(b) by 1351 days.

(21) Appl. No.: 12/202,759

(22) Filed: Sep. 2, 2008

(65) Prior Publication Data

US 2008/0318843 A1  Dec. 25, 2008

Related U.S. Application Data

(63) Continuation-in-part of application No. 11/102,454, filed on Apr. 9, 2005, now abandoned, which is a continuation-in-part of application No. 10/971,997, filed on Oct. 22, 2004, now abandoned, which is a continuation-in-part of application No. 10/821,718, filed on Apr. 9, 2004, now abandoned.

(60) Provisional application No. 60/461,354, filed on Apr. 9, 2003.

(51) Int. Cl.
*A61K 9/00* (2006.01)
*A61F 9/00* (2006.01)
*A61K 38/13* (2006.01)

(52) U.S. Cl.
CPC ............. *A61F 9/0017* (2013.01); *A61K 9/0048* (2013.01); *A61K 9/0051* (2013.01); *A61K 38/13* (2013.01)

(58) Field of Classification Search
USPC ......................................................... 424/429
See application file for complete search history.

(56) References Cited

U.S. PATENT DOCUMENTS

| | | | |
|---|---|---|---|
| 4,617,299 A | 10/1986 | Knepper | |
| 4,668,506 A | 5/1987 | Bawa | |
| 4,731,244 A | 3/1988 | Talle et al. | |
| 4,753,945 A | 6/1988 | Gilbard et al. | |
| 4,923,467 A | 5/1990 | Thompson | |
| 4,931,279 A | 6/1990 | Bawa et al. | |
| 4,939,135 A | 7/1990 | Robertson et al. | |
| 4,973,466 A | 11/1990 | Reich | |
| 4,981,841 A | 1/1991 | Gibson | |
| 4,983,580 A | 1/1991 | Gibson | |
| 5,053,388 A | 10/1991 | Gibson et al. | |
| 5,104,408 A | 4/1992 | Thompson | |
| 5,124,155 A | 6/1992 | Reich | |
| 5,124,392 A | 6/1992 | Robertson et al. | |
| 5,156,622 A | 10/1992 | Thompson | |
| 5,171,318 A | 12/1992 | Gibson et al. | |
| 5,192,535 A | 3/1993 | Davis et al. | |
| 5,196,027 A | 3/1993 | Thompson et al. | |
| 5,212,168 A | 5/1993 | Schwartz | |
| 5,271,939 A | 12/1993 | Robertson et al. | |
| 5,358,706 A | 10/1994 | Martin et al. | |
| 5,360,611 A | 11/1994 | Robertson et al. | |
| 5,401,509 A | 3/1995 | Robertson et al. | |
| 5,401,510 A | 3/1995 | Robertson et al. | |
| 5,433,745 A | 7/1995 | Graham et al. | |
| 5,472,703 A | 12/1995 | Vanderlaan et al. | |
| 5,525,349 A | 6/1996 | Robertson et al. | |
| 5,550,188 A | 8/1996 | Rhee et al. | |
| 5,565,519 A | 10/1996 | Rhee et al. | |
| 5,573,775 A | 11/1996 | Robertson et al. | |
| 5,580,570 A | 12/1996 | Robertson et al. | |
| 5,582,835 A | 12/1996 | Robertson et al. | |
| 5,589,184 A | 12/1996 | Robertson et al. | |
| 5,589,185 A | 12/1996 | Robertson et al. | |
| 5,597,381 A | 1/1997 | Rizzo, III | |
| 5,607,688 A | 3/1997 | Cejkova et al. | |
| 5,616,502 A | 4/1997 | Haugland et al. | |
| 5,665,373 A | 9/1997 | Robertson et al. | |
| 5,695,509 A | 12/1997 | El Hage | |
| 5,723,131 A | 3/1998 | Schultz et al. | |
| 5,733,563 A | 3/1998 | Fortier | |
| 5,767,079 A | 6/1998 | Glaser et al. | |
| 5,811,446 A | 9/1998 | Thomas | |
| 5,814,329 A * | 9/1998 | Shah | 424/433 |
| 5,836,313 A | 11/1998 | Perez et al. | |
| 5,932,205 A | 8/1999 | Wang et al. | |
| 5,942,487 A | 8/1999 | Ogawa et al. | |
| 5,973,089 A | 10/1999 | Meijs et al. | |

(Continued)

FOREIGN PATENT DOCUMENTS

EP  0219208  6/1992
EP  0782016 A2  7/1997

(Continued)

OTHER PUBLICATIONS

Kato (Feasibility of Drug Delivery to the Posterior Pole of the Rabbit Eye with an Episcleral Implant, Investigative Ophthalmology & Visual Science—vol. 45, No. 1, Jan. 2004).*

(Continued)

*Primary Examiner* — Adam C Milligan
(74) *Attorney, Agent, or Firm* — Finch & Maloney PLLC

(57) ABSTRACT

Hydrogel lenses are infused with a drug for the treatment of posterior segment disease. The lenses are placed in contact with the subject's cornea. Drugs can be passively released from the hydrogel and can migrate around the globe of the eye to the posterior segment.

23 Claims, No Drawings

(56) References Cited

U.S. PATENT DOCUMENTS

| | | | |
|---|---|---|---|
| 6,051,698 A | 4/2000 | Janjic et al. |
| 6,063,116 A | 5/2000 | Kelleher |
| 6,124,273 A | 9/2000 | Drohan et al. |
| 6,129,928 A | 10/2000 | Sarangapani et al. |
| 6,143,315 A | 11/2000 | Wang et al. |
| 6,201,065 B1 | 3/2001 | Pathak et al. |
| 6,201,164 B1 | 3/2001 | Wulff et al. |
| 6,248,715 B1 | 6/2001 | Rosenberg et al. |
| 6,261,545 B1 | 7/2001 | Okamoto |
| 6,268,341 B1 | 7/2001 | Rosenberg et al. |
| 6,277,365 B1 | 8/2001 | Ellis et al. |
| 6,277,855 B1 | 8/2001 | Yerxa |
| 6,331,309 B1 | 12/2001 | Jennings, Jr. et al. |
| 6,410,045 B1 | 6/2002 | Schultz et al. |
| 6,426,335 B1 | 7/2002 | Janjic et al. |
| 6,489,305 B1 | 12/2002 | Demers |
| 6,566,398 B1 | 5/2003 | Ueno |
| 6,624,203 B1 | 9/2003 | Smith |
| 6,645,978 B1 | 11/2003 | Gamache et al. |
| 6,645,994 B1 | 11/2003 | Gamache |
| 6,659,985 B2 | 12/2003 | Connor |
| 6,825,232 B2 | 11/2004 | Gamache |
| 7,169,406 B2 | 1/2007 | Schultz |
| 7,618,643 B2 | 11/2009 | Schultz |
| 2001/0046518 A1 | 11/2001 | Sawhney |
| 2002/0197300 A1 | 12/2002 | Schultz et al. |
| 2003/0069560 A1 | 4/2003 | Adamis et al. |
| 2003/0170209 A1 | 9/2003 | Abitbol |
| 2003/0203032 A1 | 10/2003 | Schultz |
| 2004/0071761 A1 | 4/2004 | Miller et al. |
| 2004/0121968 A1 | 6/2004 | Ljubimov et al. |
| 2004/0198829 A1 | 10/2004 | Sponsel et al. |
| 2005/0074497 A1 | 4/2005 | Schultz |
| 2005/0208102 A1 | 9/2005 | Schultz |
| 2005/0255144 A1 | 11/2005 | Schultz |
| 2006/0040980 A1 | 2/2006 | Lind et al. |
| 2008/0318843 A1 | 12/2008 | Schultz et al. |

FOREIGN PATENT DOCUMENTS

| | | |
|---|---|---|
| EP | 0958831 A1 | 11/1999 |
| EP | 0719545 | 6/2002 |
| WO | 9513765 | 3/1995 |
| WO | 03024420 | 3/2003 |
| WO | 03092665 | 11/2003 |
| WO | 2005082399 | 9/2005 |

OTHER PUBLICATIONS

Aiello et al., Suppression of retinal neovascularization in vito by inhibition of vascular endothelial growth factor (VEGF) using soluble VEGF-receptor chimeric proteins, Proc. Natl. Acad. Sci. USA, Nov. 1995, pp. 10457-10461, vol. 92.
Clark et al., A Vascular Endothelial Growth Factor Antagonist Is Produced by the Human Placenta and Released into the Maternal Circulation, Biology of Reproduction, 1998, pp. 1540-1548, vol. 59.
Duh et al., Vascular Endothelial Growth Factor and Diabetes—The Agonist Versus Antagonist Paradox, Diabetes—Perspectives in Diabetes, 8 pages, Oct. 1999, vol. 48.
Flieger et al., Dramatic improvement in hereditary hemorrhagic telangiectasia after treatment with the vascular endothelial growth factor (VEGF) antagonist bevacizumab, Ann Hematol—Letter to the Editor, 2006, pp. 631-632, vol. 85.
Hazzard et al., Injection of Soluble Vascular Endothelial Growth Factor Receptor 1 into the Preovulatory Follicle Disrupts Ovulation and Subsequent Luteal Function in Rhesus Monkeys, Biology of Reproduction, 2002, pp. 1305-1312, vol. 67.
Hetian et al., A Novel Peptide Isolated from a Phage Display Library Inhibits Tumor Growth and Metastasis by Blocking the Binding of Vascular Endothelial Growth Factor to Its Kinase Domain Receptor, The Journal of Biological Chemistry, Nov. 8, 2002, pp. 43137-43142, vol. 277, No. 45.
Gel, Wikipedia, http:/en.wikipedia.org/wiki/Hydrogel, downloaded from Internet Sep. 26, 2009, 5 pages.
Inoue et al., Identification of a vascular endothelial growth factor (VEGF) antagonist, sFlt-1, from a human hematopoietic cell line NALM-16, Federation of European Biochemical Societies, Letters, 2000, pp. 14 18, vol. 469.
Kimura et al., Vascular Endothelial Growth Factor Antagonist Reduces Brain Edema Formation and Venous Infarction, Journal of the American Heart Association—Stroke, May 5, 2005, pp. 1259-1263, vol. 36.
Ozaki et al., Blockade of Vascular Endothelial Cell Growth Factor Receptor Signaling Is Sufficient to Completely Prevent Retinal Neovascularization, American Journal of Pathology, Feb. 2000, 11, pages, vol. 156, No. 2.
Pisano et al., Undersulfated, low-molecular-weight glycol-split heparin as an antiangiogenic VEGF antagonist, Glycobiology, 2005, pp. 1C-6C, vol. 15, No. 2.
Schuch et al., In vivo administration of vascular endothelial growth factor (VEGF) and its antagonist, soluble neuropilin-1, predicts a role of VEGF in the progression of acute myeloid leukemia in vivo, NeoPlasia, Blood, Dec. 15, 2002, 7 pages, vol. 100, No. 13.
Siemeister et al., An antagonistic vascular endothelial growth factor (VEGF) variant inhibits VEGF-stimulated receptor autophosphorylation and proliferation of human endothelial cells, Proc. National Academy of Sciences USA, Apr. 1998, pp. 4625-4629, vol. 95.
Soker et al., Inhibition of Vascular Endothelial Growth Factor (VEGF)-induced Endothelial Cell, Proliferation by a Peptide Corresponding to the Exon 7-Encoded Domain of VEGF-165, The Journal of Biological Chemistry, Dec. 12, 1997, pp. 31582-31588, vol. 272 No. 50.
US Office Action dated Mar. 20, 2009 issued in U.S. Appl. No. 11/102,454, 27 pages.
US Office Action dated Jun. 10, 2009 issued in U.S. Appl. No. 10/971,997, 7 pages.
US Office Action dated Sep. 30, 2009 issued in U.S. Appl. No. 10/821,718, 31 pages.
US Office Action dated Nov. 4, 2009 issued in U.S. Appl. No. 11/102,454, 13 pages.
U.S. Office Action dated Dec. 24, 2009 issued in U.S. Appl. No. 10/971,997, 10 pages.
Lei Zhang et al., Angiogenic Inhibition Mediated by a DN Azyme That Targets Vascular Endothelial Growth Factor Receptor 2, Cancer Research, Oct. 1, 2002, pp. 5463-5469, vol. 62.
Del Amo et al., Current and future ophthalmic drug delivery systems—A shift to the posterior segment, Drug Discovery Today, Feb. 2008, 9 pages, vol. 12, Nos. 3/4.
Fattal et al., Ocular delivery of nucleic acids: antisense oligonucleotides, aptamers and siRNA, Science Direct, Advanced Drug Delivery Reviews, 2006, pp. 1203-1223, vol. 58.
Myles et al., Recent progress in ocular drug delivery for posterior segment disease; Emphasis on transscleral iontophoresis, Science Direct, Advanced Drug Delivery Reviews, 2005, pp. 2063-2079, vol. 57.
Callegan, et al., "Bacterial Endophthalmitis: Epidemiology, Therapeutics, and Bacterium-Host Interactions," Clinic Microbiology Reviews, vol. 15, No. 1, Jan. 2002, pp. 111-124.
Colthurst et al, 'Biomaterials used in the posterior segment of the eye', Biomaterials 21, 2000, pp. 649-665.
Gerkowicz et al, 'Studies on the use of desferrioxamine in experimental ocular siderosis produced by extrabulbar administratoin of iron', Graefe's Archive for Clinical and Experimental Ophthalmology, 1985, 5pgs, 223:101-105.
International Search Report and Written Opinion dated Aug. 25, 2006, 13 pages.
International Preliminary Search Report and Written Opinion dated Oct. 11, 2006, 10 pages.
Motely et al, 'Pseudomonas Aeruginosa Endogenous Endophthalmitis with Choroidal Abdcess in a Patient with Cystic Fibrosis', Clinicopathologic Correlation, Retina, The Jorunal of Retinal and Vitreous Diseases, 2005, vol. 25, No. 2, pp. 202-207.
Schmidt, "Back of the Eye: The Fifth Wave in Ophthalmology", Medical Supplies & Devices, 40 pages, SG Cowen dated Dec. 2003.

(56) References Cited

OTHER PUBLICATIONS

Schultz, "Drug and Growth Factor Delivery for the Treatment of Ocular Syndromes from Hydrogel Materials", Presented by the American Society for Microbiology Meeting in Washington DC in May 2003, Session #181, Poster #O-081.
Osborne, et al., "In Vivo and In Vitro Experiments Show that Betaxolol is a Retinal Neuroprotective Agent," Brain Research 751 (1997) pp. 113-123.
USPTO Office Action dated Oct. 26, 2007 issued in U.S. Appl. No. 10/821,718, 26 pgs.
U.S. Office Action issued in U.S. Appl. No. 10/821,718 dated Jun. 12, 2008 (9 pages).
Wijngaarden, "Inhibitors of Ocular Neovascularization", American Medical Association, vol. 293, No. 12, (Mar. 23, 2005),1509-1512.
Chinese Office Action dated Oct. 10, 2008 with English language translation issued in Chinese Application No. 200580012215.4, 14 pages.
US Office Action dated Oct. 16, 2008 issued in U.S. Appl. No. 10/971,997, 16 pages.
Dua and Azuara-Bianco, "Amniotic Membrane Transplantation," Br. J. Ophthalmol, 83:748-752 (1999).
Hillman, "Management of Acute Glaucoma with Pilocarpine-Soaked Hydrophillic Lens," Br.J.Ophthal. 58:674-679 (1974).
Lohmann et al., "Screening of Myopic Lasik Patients with Aggressive Woundhealing: Quantitative Determination of EGF mRNA in corneal Epithelial Cells," 97th Annual Meeting Germal Ophthalmological Society, K 180 Berlin Sep. 23-26, 1999.
Wang et al., "Reduction in Corneal Haze and Apoptosis by amniotic membrane Matrix in Excimer Laser Photoablation in Rabbits," J. Catract Refract. Surg. 27:310-319 (2001).
Wilson et al., "The Fas-Fas Ligand Sysem and Other Modulators of Apoptosis in the Cornea," Invest. Ophthalmology Vis. Sci. 37:1582-1592 (1996).
Woo et al., "Effects of Amniotic Membrane on Epithelial Wound Healing and Stromal Remodelling After Excimer Laser Keratectomy in Rabbit Cornea," Br. J. Opthalmol. 85:345-349 (2001).
Kim and Kim, Kor. J. Opthlmol. vol. 2:72-76 (1988).
US Office Action mailed Jul. 19, 2010 in U.S. Appl. No. 10/821,718, 35 pgs.
US Office Action mailed Jun. 14, 2010 in U.S. Appl. No. 11/102,454.
Samples, J.R., et al., Investigative Ophthalmology & Visual Science, vol. 25, 1984, pp. 843-850.
US Office Action issued Aug. 25, 2010 in U.S. Appl. No. 10/971,997, 17 pages.
US Office Action issued Feb. 25, 2014 in U.S. Appl. No. 12/948,836, 13 pages.

* cited by examiner

DEVICE AND METHOD FOR THE DELIVERY OF DRUGS FOR THE TREATMENT OF POSTERIOR SEGMENT DISEASE

CROSS-REFERENCE TO RELATED APPLICATIONS

This application is a continuation-in-part of U.S. application Ser. No. 11/102,454, filed Apr. 9, 2005, which is a continuation-in-part of U.S. application Ser. No. 10/971,997, filed Oct. 22, 2004 which is a continuation-in-part of U.S. application Ser. No. 10/821,718, filed Apr. 9, 2004, which claims benefit of U.S. Provisional Application No. 60/461,354, filed Apr. 9, 2003. Each of these applications is hereby incorporated by reference herein.

BACKGROUND OF THE INVENTION

In general, the invention relates to the fields of hydrogels, drug delivery systems, the treatment of eye disease and, in particular, posterior segment diseases.

Systemic and topical (e.g., via eye drops) administration of drugs for treatment of diseases of the posterior segment of the eye, such as macular degeneration, are often undesirable. These methods typically require higher total doses of the drug because these routes are inefficient at delivering the drug to the posterior segment. Such high doses increase the cost and may also cause side effects such as local inflammation or adverse systemic reactions. In addition, for most topical treatments, the drug is quickly washed out of the eye, limiting the effective time of treatment.

Thus, sustained-release delivery devices that would continuously administer a drug to the eye for a prolonged period of time are desired for the treatment of posterior segment diseases.

SUMMARY OF THE INVENTION

The present invention features hydrogel drug delivery systems and methods of producing and using such systems for the treatment of disease in the posterior segment of the eye, e.g., the vitreous, retina (including the macula), choroids, sclera, and optic nerve. The systems are based on a hydrogel into which one or more drugs can be passively transferred from a dilute solution, e.g., an aqueous solution. When placed in contact with eye tissue, the drug or drugs passively transfer out of the hydrogel to provide treatment of posterior segment diseases. The drugs can be transported around the globe of the eye to the posterior segment without significant entry into the vitreous or the systemic circulatory system.

Accordingly, in one aspect, the invention features a polymeric hydrogel that contains a drug for the treatment of a posterior segment disease, wherein the drug is capable of being passively released in a therapeutically effective amount to treat the posterior segment disease. Exemplary hydrogel materials include a tetrapolymer of hydroxymethylmethacrylate, ethylene glycol, dimethylmethacrylate, and methacrylic acid. Other examples of hydrogels include etafilcon A, vifilcon A, lidofilcon A, vasurfilcon A, and polymacon B. In addition, variations of these polymers formed by the use of different packing solutions (e.g., phosphate-buffered saline and boric acid) in the manufacturing process are also included. The hydrogel may be ionic or non-ionic. In various embodiments, the drug is capable of being passively released into the ocular environment under ambient or existing conditions. In other embodiments, the hydrogel may be shaped as a contact lens, e.g., one capable of correcting vision. Such a contact lens may be capable of correcting vision in the range of +8.0 to −8.0 diopters or may be piano. The contact lens may also have a base curve between 8.0 and 9.0.

The invention further features a method for making a hydrogel drug delivery system by placing the hydrogel, e.g., a contact lens, in a solution containing one or more drugs as described herein, which is passively transferred to the hydrogel. This method may further include the steps of washing the hydrogel in an isotonic saline solution and partially desiccating the hydrogel prior to placement in the solution. The solution may have, e.g., a pH between 6.9 and 7.4, and a drug concentration of between 0.00001 and 10%. In one embodiment, the hydrogel is placed in the solution of drug for at least 30 minutes.

In another aspect, the invention features a method for treating a posterior segment disease. The method includes placing a hydrogel, as described herein, in contact with an eye, wherein the drug or drugs are passively released from the hydrogel to treat the disease. In various embodiments, the posterior segment disease is in the vitreous, retina (e.g., the macula), choroids, sclera, or optic nerve. The hydrogel may passively release, for example, at least 0.0001, 0.0005, 0.001, 0.005, 0.01, 0.05, 0.1, 0.5, 1, 10, 15, 20, 50, 75, 100, 250, 500, or 1000 µg of a drug, and the hydrogel may be placed in contact with the eye for at least 0.5, 1, 1.5, 2, 2.5, 3, 3.5, 4, 4.5, 5, 7.5, 10, 15, or 24 hours.

Exemplary drugs and posterior segment diseases are described herein.

As used herein, by "ambient conditions" is meant room temperature and pressure.

By "existing conditions" is meant in situ in the eye.

By "treating" is meant medically managing a patient with the intent that a prevention, cure, stabilization, or amelioration of the symptoms will result. This term includes active treatment, that is, treatment directed specifically toward improvement of the disease; palliative treatment, that is, treatment designed for the relief of symptoms rather than the curing of the disease; preventive treatment, that is, treatment directed to prevention of the disease; and supportive treatment, that is, treatment employed to supplement another specific therapy directed toward the improvement of the disease. The term "treating" also includes symptomatic treatment, that is, treatment directed toward constitutional symptoms of the disease.

By "ocular environment" is meant the tissues of and surrounding the eye, including, for example, the sclera, cornea, and other tissues of the ocular cavity and the posterior segment.

The "posterior segment" of the eye includes the retina (including the macula), choroids, sclera, and optic nerve.

Exemplary posterior segment diseases include retinal detachment, diabetic retinopathy, macular degeneration (e.g., age-related), proliferative vitreoretinopathy, endophthalmitis, retinopathy of prematurity, posterior segment trauma, intraocular lens-related posterior segment complications, retinal vascular diseases, macular edema, intraocular tumors, hereditary retinal degenerations, AIDS-related retinitis, posterior segment uveitis, and systemic diseases with retinal manifestations. For the purposes of this invention, glaucoma is not a posterior segment disease.

All percentages described in the present invention are by weight unless otherwise specified.

Other features and advantages of the invention will be apparent from the following description and the claims.

DETAILED DESCRIPTION OF THE INVENTION

This invention provides a polymeric drug delivery system including a hydrogel containing one or more drugs for the treatment of a posterior segment disease. Allowing passive transference of this drug from a dilute solution into the hydrogel produces the delivery system. The hydrogel, when placed in contact with the eye, delivers the drug. The delivery of the drug can be sustained over an extended period of time, which is of particular utility in the eye, which is periodically flushed with tears. This sustained delivery may accelerate the treatment process while avoiding potential damaging effects of localized delivery of high concentrations of drugs compared to, e.g., intravitreal injection.

Posterior Segment Diseases

Posterior segment diseases to be treated include, for example, retinal detachment, neovascularization, diabetic retinopathy, macular degeneration (e.g., age-related), proliferative vitreoretinopathy, endophthalmitis, retinopathy of prematurity, posterior segment trauma, intraocular lens-related posterior segment complications, retinal vascular diseases, macular edema (e.g., diabetic), intraocular tumors, retinal degeneration (e.g., hereditary), vascular retinopathy, inflammatory diseases of the retina, AIDS-related retinitis, uveitis, and systemic diseases with retinal manifestations. Neovascularizations include retinal, choroidal, and vitreal. The retinal neovascularization to be treated can be caused by diabetic retinopathy, vein occlusion, sickle cell retinopathy, retinopathy of prematurity, retinal detachment, ocular ischemia, or trauma. The intravitreal neovascularization to be treated can be caused by diabetic retinopathy, vein occlusion, sickle cell retinopathy, retinopathy of prematurity, retinal detachment, ocular ischemia, or trauma. The choroidal neovascularization to be treated can be caused by retinal or subretinal disorders of age-related macular degeneration, diabetic macular edema, presumed ocular histoplasmosis syndrome, myopic degeneration, angioid streaks, or ocular trauma. Other posterior segment diseases are known in the art.

Drug Delivery System

Hydrogels. This invention may employ different polymer compositions. For example, conventional soft contact lenses can be used and can be either ionic or non-ionic hydrogels containing between 10% and 90%, e.g., 24% or 37.5% to 65% or 75%, water by weight and can have any base curve, e.g., from 8.0 to 9.0. The contact lenses may also have the ability to correct vision, for example, over a range of diopters of +8.0 to −8.0. Exemplary hydrogel contact lens materials include etafilcon A, vifilcon A, lidofilcon A, polymacon B, vasurfilcon A, and a tetrapolymer of hydroxymethylmethacrylate, ethylene glycol, dimethylmethacrylate, and methacrylic acid. These materials may also be employed, in other physical forms. Other suitable hydrogel materials are known to those skilled in the art. The hydrogels may be insoluble or may dissolve over time in vivo, e.g., over one day or one week. The drug is passively delivered, for example, by diffusion out of the hydrogel, by desorption from the hydrogel, or by release as the hydrogel dissolves.

The drug delivery system may be produced from a partially desiccated hydrogel (or equivalently a partially hydrated hydrogel). The desiccation step removes, for example, approximately 5%, 10%, 15%, 20%, 25%, 30%, 40%, 50%, 60%, or 75% of the water in the hydrogel. Desiccation can occur, for example, by exposure of the hydrogel to ambient or humidity controlled air, by heating the hydrogel for a specific period of time, or by blowing dried gas, such as $N_2$, over the hydrogel. In one embodiment, the hydrogel is saturated with physiological (isotonic) saline prior to desiccation. The partially desiccated hydrogel is then soaked, e.g., for at least 30 minutes, in a dilute solution of drug, e.g., at a pH between 6.9 to 7.4. In certain embodiments, the drug is transferred to a contact lens from a non-aqueous solvent, e.g., dimethyl sulfoxide, which may be at least partially removed and replaced with an aqueous solution prior to use in a patient. The hydrogels may also be soaked for at least 1 hour, 6 hours, 12 hours, or 24 hours. The concentration of drug into which the hydrogel is placed is typically 0.000001, 0.000005, 0.00001, 0.00005, 0.0001, 0.0005, 0.001, 0.005, 0.01, 0.05, 0.1, 0.5, 1, 5, 10, 15, 20, 50, 75, 100, 250, 500, or 1000 µg/mL. Higher concentrations may also be used, for example, to reduce the soaking time. The drug is passively transferred into the hydrogel. This transfer may occur at least in part by rehydrating the hydrogel. Diffusion of the drug into the water or polymer in the hydrogel may also occur. In alternative embodiments, a fully hydrated or fully desiccated hydrogel is placed in the soaking solution to produce the medicated hydrogel.

Desirably, the concentration of drug transferred to the hydrogel is substantially lower than the solution in which the hydrogel is soaked. For example, the concentration of growth factor in the hydrogel is at least 2×, 5×, or 10× less than that of the soaking solution. Some drugs, however, may have a higher affinity for a hydrogel than the soaking solution, and such a hydrogel will have a higher concentration of drug than the solution in which it was soaked, e.g., at least 2×, 5×, or 10× more. The water content and type of hydrogel, time and conditions, e.g., temperature of soaking, composition of the soaking solution (e.g., ionic strength and pH), and type of drug employed also may influence the concentration of drug in the drug delivery system. Since the water content of the hydrogel may also help to determine the total amount of drug present in a hydrogel, it represents a variable by which to control the amount of drug delivered to a tissue. The production of a hydrogel containing a specified amount of drug can be accomplished by routine experimentation by one skilled in the art.

The use of preservatives is non-ideal as they may transfer to a hydrogel at a disproportionately high concentration and cause cytotoxicity.

Treatment Approaches

To treat a posterior segment disease, the hydrogels of the invention are contacted with the cornea of an individual. The hydrogels may be employed in an open or closed eye period. When the system is shaped as a contact lens, the lens may simply be placed in the eye normally in order to deliver the drug. The hydrogel may also be part of a bandage or may be adhered (e.g., by adhesives or sutures) to the eye. If the hydrogel is placed internally in a patient, the hydrogel is advantageously biodegradable. The time period over which a hydrogel lens is worn may depend on the level of treatment desired or the amount of drug in the lens. Hydrogels may be considered to be disposable and may be replaced after a specified period of time, e.g., at least 0.5, 1, 1.5, 2, 2.5, 3, 3.5, 4, 4.5, 5, 7.5, 10, 15, or 24 hours. Alternatively, a hydrogel that has a depleted amount of drug may be recycled by soaking the hydrogel again in a solution of drug.

The methods of treatment described herein are capable of delivering a drug to the ocular environment of a patient for a period of time longer than the dwell time achievable by gels or drops. The convenience and simplicity of this system would in many cases enhance patient compliance with therapy.

In certain embodiments, at least 0.001, 0.005, 0.01, 0.05, 0.1, 0.5, 1, 5, 10, 15, 20, 50, 75, 100, 200, 500, 750, or 1000 µg of the drug is released from the hydrogel. This delivery occurs by passive transfer and allows medications to be delivered to the posterior segment. The use of hydrogels of the invention may also allow patients to be treated using fewer applications than with traditional methods. In addition, the drug may be released from the hydrogel at a more rapid rate than the release of the drug into a fixed volume of fluid because as the eye produces tears, the drug released is flushed away from the site of application causing an increase in the relative rate of diffusion of the drug out of the hydrogel. The replenishing action of fluids such as tears may also effectively increase the rate of diffusion of the drug into the fluid and lead to earlier onset of therapeutic activity.

A variety of drugs and drug precursors may be delivered to the posterior segment. In some embodiments, corticosteroids can be delivered via a hydrogel. Corticosteroids (or corticoids) are any steroids (lipids that contain a hydrogenated cyclopentoperhydrophenanthrene ring system) elaborated by the adrenal cortex (except sex hormones of adrenal origin) in response to the release of adrenocorticotrophin or adrenocorticotropic hormone by the pituitary gland, or to any synthetic equivalent, or to angiotensin II. Corticosteroids include but may not be limited to alclometasone dipropionate, amcinonide, amcinafel, amcinagfide beclomethasone, betamethasone, betamethasone dipropionate, betamethasone valerate, clobetasone propionate, chloroprednisone, clocortolone, cortisol, cortisone, cortodoxone, difluorosone diacetate, descinolone, desonide difluprednate, dihydroxycortisone, desoximtasone, dexamethasone, deflazacort, diflorasone diacetate, dichlorisone, esters of betamethasone, flucetonide, flucloronide, fluorocortisone, flumethasone, flunisolide, fluocinonide, fluocinolone acetonide, flucortolone, fluperolone, fluprednisolone, fluroandrenolone acetonide, fluocinolone acetonide, flurandrenolide, fluorametholone, fluticasone propionate, hydrocortisone, hydrocortisone butyrate, hydrocortisone valerate, hydrocortamate, medrysone, meprednisone, methylprednisone, methylprednisolone, mometasone furoate, paramethasone, prednisone, prednisolone, prednisone, triamcinolone acetonide, and triamcinolone.

In one set of embodiments, short term action corticosteroids can be passively transferred from a hydrogel lens around the globe to the posterior segment. Short term action corticosteroids, as used herein, means agents that are metabolized in situ within 2-4 hours. These drugs include beclomethasone, prednisolone, prednisone, fluticasone, budesonide, betamethasone dipropionate, amelometasone, mometasone and ciclesonide. Derivatives of these drugs may also be used. Derivatives include active salts or acids and/or precursors that can metabolize into active compounds. By administering short term drugs via hydrogel, the benefits of the drug may be maximized while reducing or eliminating undesirable side effects. Passive release of a compound from a hydrogel can provide for a consistent dosing concentration at the target (posterior segment or anterior segment) even if the compound is metabolized quickly. Because the compound is provided directly to the posterior segment, effects on the vitreous humor, such as elevated intraocular pressure, can be reduced or eliminated. Specific hydrogels and specific concentrations of drugs in hydrogels can be readily determined by those of skill in the art when provided with details regarding the drug, the subject, and the condition being treated.

Hydrogels may also be used to deliver intermediate and long acting corticosteroids. For these compounds, total contact time and frequency of contact time may be less than with short acting compounds. A significant portion of the compound stored in the hydrogel can be delivered to the posterior segment and can be helpful in avoiding undesirable side effects. In some instances, greater than 50%, greater than 75% or greater than 90% of the drug carried by the hydrogel can be delivered to the posterior segment.

In another embodiment, medicaments that include vitamins or growth factors may be delivered via a hydrogel. Such compounds may have activity in the anterior or posterior segment of the eye. This may include fat soluble and/or water soluble vitamins. Fat soluble vitamins include, for example, Vitamin A and Vitamin E. Derivatives of these vitamins include active salts thereof.

In another embodiment, medicaments may be steroids selected from classes of steroids including estrogens, androgens, progestagens, glucocorticoids, mineralocorticoids, phytosterols, ergosterols and derivatives thereof.

In another embodiment, the medicament may be chosen from the group consisting of squalene, lanosterol, cholesterol, pregnenolone, 17-hydrosypregnenolone, DHEA, androstenedione, androstanediol and derivatives thereof.

In another embodiment, the medicament may be selected from the group consisting of prednisone, prednisolone, methylprednisolone, betamethasone, dexamethasone, triamcinolone, hydrocortisone, aldosterone, squalene, lanosterol, cholesterol, pregnenolone, 17-hydroxypregnenolone, DHEA, androstenedione, androstanediol, estradiol, estriol, estrone, testosterone, dihydrotestosterone, androsterone, progesterone, 17-hydroxyprogesterone, progestins, cortisol, prednisone, stigmasterol, brassicasterol, ergosterol, ergocalciferol and derivatives thereof.

In another embodiment, the drug may comprise an anti-inflammatory compound. Anti-inflammatory compounds that may be useful include, for example, cyclosporin, sirolimus, rapamycin, cyclophilin A, B, or D inhibitors and derivatives thereof.

Hydrogels may in the form of a contact lens and may be placed on the cornea in a conventional manner. Hydrogels including a drug or drug precursor may be kept in contact with the eye for short or extended periods. For instance, contact times may be greater than one minute, greater than 1 hour, greater than six hours, greater than 12 hours, greater than 1 day or greater than 7 days. Likewise, contact times may be less than one week, less than one day, less than 12 hours or less than six hours. In some embodiments it may be desirable to administer a compound to the posterior segment for only a portion of the 24 hour day or for several different portions of the day. Unlike vitreal injection and other invasive techniques, hydrogels allow for fine tuning of drug administration times. In some cases, the subject can place and remove the hydrogel at various time intervals without supervision or aid from medical personnel. The same hydrogel lens may be placed in contact with the eye one, two, three or more times. For instance, a lens may be contacted with the eye for a first time period and then removed for a second time period before being replaced for a third time period. In some embodiments, specific times of day may be chosen for contact with the subject's eye. For example, a hydrogel lens may be used at night while the subject sleeps and may be removed during the day.

The concentration of a drug that is to be used in a hydrogel is a function of several parameters including the effective concentration at the posterior segment, the rate of release from the hydrogel and the percentage of the released compound that is delivered to the posterior segment. Rate of release is a function of several factors, including the composition of the hydrogel, the composition of the aqueous component of the hydrogel, the kinetic properties of the drug itself and the environment on the cornea of the subject's eye to be treated. Appropriate quantities to infuse into a hydrogel can be facilitated by knowing what the effective dose at the posterior segment is in combination with the knowledge that a significant portion of the drug will be delivered directly to the posterior segment. Typically, these quantities can be determined by routine experimentation.

In some embodiments, such as with classes of corticosteroids, a single hydrogel contact lens may be loaded with about 1 mg of active compound. For instance, experiments have shown that an effective concentration of beclomethasone can be delivered to the posterior segment by treating with a lens that includes about 700 ng of the compound. For prednisolone, 450 ng per lens has been shown to be effective. In each case, about 95% of the drug exited the lens after 2 hours of contact with the cornea. It is believed that the consistent pore size of the hydrogels provides for a consistent delivery rate of a variety of compounds.

To incorporate a compound into a hydrogel, the compound may be provided as a suspension or solution in, for example, water for injection or saline for injection. The compound of interest can be incorporated into the lens by placing it in the solution for a period of several hours. The lens may be partially desiccated by exposing it to air for a short period prior to immersion into the suspension. Results show that with a 1 mL suspension volume and with suspension concentration in the range of from 1 to 5 mg/L that with gentle agitation about 0.07% of the compound is incorporated into the lens after a 3 hour period. Higher concentrations of the compound in the solution and/or longer immersion times do not appear to increase the amount of compound that is infused into the lens.

In one aspect, a method is provided in which a drug can be delivered via a hydrogel lens directly to the posterior segment without significant passage through the vitreous of the eye or through the subject's circulatory system. This pathway can provide important advantages due to the direct delivery to the afflicted segment without entry into the vitreous or the systemic circulatory system. Drugs used for the treatment of posterior segment disease are often introduced via vitreal injection. These methods of delivery may have deleterious effects on portions of the eye that are not the target for treatment. For instance, drugs such as corticosteroids may cause an increase in intraocular pressure that may require additional treatment or may require a reduction in the administration of the drug. By circumventing the vitreous, direct delivery of a drug to the posterior segment around the eye globe can reduce or eliminate these side effects.

The data below indicate that drugs can be delivered passively from a contact lens to the posterior segment (including the retina, macula and optic nerve) by passing around the globe of the eye without significant entry into the vitreous or the subject's systemic circulatory system. The pathway of delivery is believed to be through one or more of three different routes. The first is through the circulatory system of the eye, which is isolated from the rest of the circulatory system of the subject. The second pathway is through the nerve system of the eye, and the third pathway is through the musculature that surrounds the eye and penetrates to the posterior segment.

A series of experiments were designed to determine the efficacy of delivery to the posterior segment from a hydrogel positioned on the cornea. The experiments also measured the amount of drug found in the vitreous humor and in the blood plasma (indicating systemic involvement).

In the first experiment, rabbits were treated by placing hydrogel lenses on the corneas of the animals for a period of 3 hours. Each lens was infused with about 450 ng of prednisolone incorporated therein. The lenses were placed onto the eyes of anesthetized animals (closed eye period) for the three hour period after which time the lenses were removed. The procedure was repeated about every other day or every three days until 5 applications had been completed.

After completion of the five applications, each eye of the animal was analyzed for prednisolone concentration using LC/MS/MS. The portion of the posterior segment that was analyzed included macula, retina, surrounding muscle, nerve and circulatory, including connective tissues and cells. Sample size typically was about 800 mg. Table 1 provides data for prednisolone concentrations measured in the posterior segment as well as in the aqueous humor. Table 2 provides data for prednisone using the same samples as for Table 1. The limit of quantification for prednisolone was 0.5 ng/mL and for prednisone was 0.05 ng/mL. A data point of "BLOQ" indicates non-detectable levels of the compound were found for that data point.

In a second experiment, a different set of rabbit subjects were treated by placing contact lenses infused with about 700 ng beclomethasone onto each cornea. The procedure was identical to that for prednisolone as described above. Table 3 provides beclomethasone concentrations found in the posterior segment as well as in the vitreous humor. Table 4 provides data for 17-Beclomethasone mono-proprionate, a desirable metabolite of beclomethasone. The data generated for tables 3 and 4 are from the same samples. The limit of quantification for both beclomethasone and 17-beclomethasone mono-proprionate was 0.05 ng/mL. A data point of "BLOQ" indicates non-detectable levels of the compound.

TABLE 1

Prednisolone

| Animal Number | Eye | Posterior Segment Concentration (ng/G) | Vitreous Humor Concentration (ng/mL) |
|---|---|---|---|
| A1 (5) | OS | 74.8 | BLOQ |
| A1 (5) | OD | 26.8 | BLOQ |
| A2 (5) | OS | 166 | BLOQ |
| A2 (5) | OD | 40.8 | BLOQ |
| C2 (5) | OS | 130 | BLOQ |
| C2 (5) | OD | 113 | BLOQ |
| C3 (2) | OS | 31.2 | BLOQ |
| C3 (2) | OD | 26.0 | BLOQ |

TABLE 2

Prednisone

| Animal Number | Eye | Posterior Segment Concentration (ng/G) | Vitreous Humor Concentration (ng/mL) |
|---|---|---|---|
| A1 (5) | OS | BLOQ | 0.219 |
| A1 (5) | OD | BLOQ | BLOQ |
| A2 (5) | OS | BLOQ | BLOQ |
| A2 (5) | OD | BLOQ | BLOQ |
| C2 (5) | OS | BLOQ | 0.147 |
| C2 (5) | OD | BLOQ | BLOQ |
| C3 (2) | OS | BLOQ | BLOQ |
| C3 (2) | OD | BLOQ | BLOQ |

TABLE 3

Beclomethasone

| Animal Number | Eye | Posterior Segment Concentration (ng/G) | Vitreous Humor Concentration (ng/mL) |
|---|---|---|---|
| B1 (5) | OS | BLOQ | BLOQ |
| B1 (5) | OD | 1.55 | BLOQ |

TABLE 3-continued

Beclomethasone

| Animal Number | Eye | Posterior Segment Concentration (ng/G) | Vitreous Humor Concentration (ng/mL) |
|---|---|---|---|
| B2 (5) | OS | 27 | BLOQ |
| B2 (5) | OD | 6.54 | BLOQ |
| C4 (5) | OS | BLOQ | BLOQ |
| C4 (5) | OD | BLOQ | BLOQ |
| B3 (2) | OS | 12.1 | BLOQ |
| B3 (2) | OD | 9.3 | BLOQ |

TABLE 4

17-Beclomethasone mono-proprionate

| Animal Number | Eye | Posterior Segment Concentration (ng/G) | Vitreous Humor Concentration (ng/mL) |
|---|---|---|---|
| B1 (5) | OS | 3.94 | BLOQ |
| B1 (5) | OD | 9.2 | 0.727 |
| B2 (5) | OS | 57.8 | BLOQ |
| B2 (5) | OD | 23.6 | 0.107 |
| C4 (5) | OS | 1.26 | 0.0678 |
| C4 (5) | OD | 1.64 | BLOQ |
| B3 (2) | OS | 29.4 | 0.190 |
| B3 (2) | OD | 80.8 | 0.0584 |

As can be seen from the results provided in Table 1 there was significant delivery of prednisolone to the posterior segment. The average concentration of prednisolone in the posterior segment was greater than 10% of the amount provided in the hydrogel lenses (five treatments). Treatment with beclomethasone resulted in delivery of beclomethasone to the posterior segment and even greater concentrations of 17-beclomethasone mono-proprionate in the posterior segment. This indicates the formation of metabolites from the parent drug in the posterior segment. The presence of metabolites, as well as the parent compound, in the posterior segment indicates that higher doses of the drug may be delivered to obtain efficacious levels of both the parent compound and the metabolite. Lower dosage levels will typically be used for drugs that do not produce desirable metabolites at the posterior segment.

Although not shown in the tables, plasma analysis indicated an absence (none detected) of the four compounds in the circulatory system. Thus both the vitreous humor and the blood plasma contained less than 1% of the drug concentration present in the hydrogel at the start of treatment. Of the total amount of drug delivered to the subject from the hydrogel, more than 10% of the drug was directed to the posterior segment without detectable entry into the vitreous or the systemic circulatory system. This indicates a surprisingly targeted approach using a passive, non-invasive method of drug delivery to the posterior segment. The metabolite results also indicate that a drug precursor may be delivered from a hydrogel and can be converted to an active compound in the posterior segment itself.

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the art, are intended to be within the scope of the invention. Other embodiments are within the claims.

What is claimed is:

1. A method of delivering a drug for the treatment of a posterior segment disease to the posterior segment of the eye for the treatment of posterior segment disease in a subject, the method comprising:
   contacting a contact lens with an eye of a subject in need of treatment of posterior segment disease, the contact lens comprising the drug; wherein the drug is passively released from the contact lens and penetrates the ocular tissue and contacts the posterior segment of the eye and treats the posterior segment disease in the subject.

2. The method of claim 1 wherein the drug penetrates to the posterior segment via the eye circulatory system, the eye musculature or the eye nerve system.

3. The method of claim 1 wherein a concentration of the drug in the subject does not exceed 1% of the drug concentration in the contact lens.

4. The method of claim 1 wherein the contact lens is continuously contacted with the eye for a period of greater than 5 minutes.

5. The method of claim 1 wherein the contact lens is continuously contacted with the eye for a period of greater than 3 hours.

6. The method of claim 1 wherein the contact lens is continuously contacted with the eye for a period of greater than 24 hours.

7. The method of claim 1 wherein the contact lens is continuously contacted with the eye for a period of greater than one week.

8. The method of claim 1 wherein the drug comprises an angiogenesis inhibitor or an angiogenesis inhibitor precursor.

9. The method of claim 1 wherein the drug is selected from the group consisting of beclomethasone, prednisolone, prednisone, fluticasone, budesonide, betamethasone dipropionate, amelometasone, mometasone, ciclesonide, triamcinolone acetonide, fludrocorisone and flumethasone.

10. The method of claim 1 wherein the drug is metabolized at the posterior segment.

11. The method of claim 1 wherein the drug comprises an anti-inflammatory compound or growth factor.

12. The method of claim 1 wherein the drug comprises at least one of cyclosporin, sirolimus, rapamycin, and a cyclophilin A, B, or D inhibitor.

13. The method of claim 1 wherein the drug comprises a short acting corticosteroid.

14. The method of claim 1 wherein the drug comprises a fat soluble vitamin.

15. The method of claim 13 wherein the drug comprises vitamin A and/or vitamin E.

16. The method of claim 1 wherein the drug comprises a steroid selected from the group consisting of estrogens, androgens, progestagens, glucocorticoids, mineralocorticoids, phytosterols and ergosterols.

17. The method of claim 1 wherein the drug comprises a steroid selected from the group consisting of squalene, lanosterol, cholesterol, pregnenolone, 17-hydroxypregnenolone, DHEA, androstenedione and androstanediol.

18. The method of claim 1 wherein the drug comprises a compound selected from the group consisting of prednisone, prednisolone, methylprednisolone, betamethasone, dexamethasone, triamcinolone, hydrocortisone, aldosterone, squalene, lanosterol, cholesterol, pregnenolone, 17-hydroxypregnenolone, DHEA, androstenedione, androstanediol, estradiol, estriol, estrone, testosterone, dihydrotestosterone, androsterone, progesterone, 17-hydroxyprogesterone, progestins, cortisol, prednisone, stigmasterol, brassicasterol, ergosterol, ergocalciferol and derivatives thereof.

19. The method of claim 1 wherein the posterior segment disease is at least one of retinal detachment, diabetic retinopathy, macular degeneration, age-related macular degeneration, proliferative vitreoretinopathy, endophthalmitis, retinopathy of prematurity, posterior or anterior segment trauma intraocular lens-related posterior segment complications, retinal vascular diseases, macular edema, intraocular tumors, hereditary retinal degenerations, AIDS-related retinitis and posterior segment uveitis.

20. The method of claim 1 wherein the systemic blood concentration of the drug in the subject does not exceed 1% of the peak drug concentration in the contact lens.

21. The method of claim 1 wherein the drug comprises zinc-monocysteine.

22. The method of claim 1 wherein the concentration of the drug in the vitreous humor of the eye being treated is less than the concentration of the drug in the posterior segment at the time of peak concentration in the posterior segment.

23. The method of claim 1 further comprising limiting the delivery of the drug into the vitreous humor of the eye being treated to a first concentration that is below a second concentration that results in increased intraocular pressure in a majority of subjects.

* * * * *